United States Patent
Fors et al.

(10) Patent No.: US 8,566,122 B2
(45) Date of Patent: Oct. 22, 2013

(54) METHOD AND APPARATUS FOR NAVIGATION TO UNSEEN RADIOLOGY IMAGES

(75) Inventors: Steven Lawrence Fors, Chicago, IL (US); Christopher Janicki, Barrington, IL (US)

(73) Assignee: General Electric Company, Schenectady, NY (US)

( * ) Notice: Subject to any disclaimer, the term of this patent is extended or adjusted under 35 U.S.C. 154(b) by 665 days.

(21) Appl. No.: 12/199,013

(22) Filed: Aug. 27, 2008

(65) Prior Publication Data

US 2010/0057496 A1 Mar. 4, 2010

(51) Int. Cl.
*G06F 19/00* (2011.01)
(52) U.S. Cl.
USPC .............................................. 705/3
(58) Field of Classification Search
USPC ............... 705/2–3; 378/37; 709/219; 707/10
See application file for complete search history.

(56) References Cited

U.S. PATENT DOCUMENTS

| | | | |
|---|---|---|---|
| 7,328,186 B2 * | 2/2008 | Brattain et al. | 705/37 |
| 7,801,890 B1 * | 9/2010 | Alexander | 707/732 |
| 2001/0044837 A1 * | 11/2001 | Talib et al. | 709/219 |
| 2004/0114714 A1 * | 6/2004 | Minyard et al. | 378/37 |
| 2006/0155579 A1 * | 7/2006 | Reid | 705/2 |
| 2008/0005118 A1 * | 1/2008 | Shakib et al. | 707/10 |
| 2009/0148068 A1 * | 6/2009 | Woodbeck | 382/305 |

FOREIGN PATENT DOCUMENTS

JP 2007336283 * 6/2006

* cited by examiner

*Primary Examiner* — John Pauls
(74) *Attorney, Agent, or Firm* — Hanley, Flight and Zimmerman, LLC

(57) ABSTRACT

Certain embodiments present a system for navigating medical images of a patient file stored in an image database. An image labeler labels medical images based upon whether the images have previously been displayed on an interface. The system also provides an image search engine that searches the images based on the labels. The image search engine generates a subset of images from a larger group of medical images within a database based upon the labels. The interface includes a graphical meter that corresponds to medical images that have not previously been displayed on the interface. The graphical meter may enumerate the quantity of images that have not previously been displayed. The graphical meter may also illustrate the proportion of images that have not previously been displayed. The graphical meter may include a hyperlink that points to an image that has not previously been displayed. The graphical meter may also include a hyperlink that points to a location containing the images that have not been previously displayed.

16 Claims, 4 Drawing Sheets

METHOD AND APPARATUS FOR NAVIGATION TO UNSEEN RADIOLOGY IMAGES

BACKGROUND OF THE INVENTION

Certain embodiments of the present technology relate to viewing medical images (e.g. X-ray images, CT images, MRI images) of a patient file stored in an image database. More particularly, certain embodiments relate to methods and apparatuses for navigating to images that have not previously been viewed or seen.

In radiology, the digitization of medical imaging has resulted in great increases in the quantity of medical images available per patient file. It is difficult for medical practitioners, such as radiologists, to recall or remember which images he or she has already viewed when reviewing a patient file. As a result, medical practitioners may sometimes inadvertently fail to view one or more images of a patient file. This results in a failure of information being communicated from an image database to a medical practitioner.

Therefore, there is a need for methods and apparatuses for medical practitioners to more easily and more accurately navigate to images that have not previously been viewed and to know when all images have been viewed.

BRIEF SUMMARY OF THE INVENTION

Certain embodiments present a method and apparatus for navigating to medical images (e.g. X-ray images, CT images, MRI images) of a patient file stored in an image database. For example, certain embodiments may allow a medical practitioner, such as a radiologist, to keep track of which images of a patient file have been viewed and which have not. Additionally, certain embodiments may allow a medical practitioner to navigate directly to medical images that have not previously been viewed. Also, certain embodiments may allow a medical practitioner to know when all medical images of a patient file have been viewed.

An image labeler labels medical images based upon whether the images have previously been displayed on an interface. An image search engine that searches the images based on the labels may also be provided. The image search engine generates a subset of images from a larger group of medical images within a database based upon the labels. The interface includes a graphical meter for representing which images have and have not been previously accessed or viewed on the interface. The graphical meter may enumerate the quantity and/or proportion of images that have not previously been displayed. The graphical meter may include a hyperlink that points to an image or to a location containing the images that have not been previously displayed.

Certain embodiments of the present application provide a technical effect of automatically labeling accessed or viewed images upon accessing or viewing. Certain embodiments provide a technical effect of introducing a graphical meter that shows which images have and have not been accessed or viewed, and that offers a navigation device to quickly launch images that have not been viewed.

Figure 1:
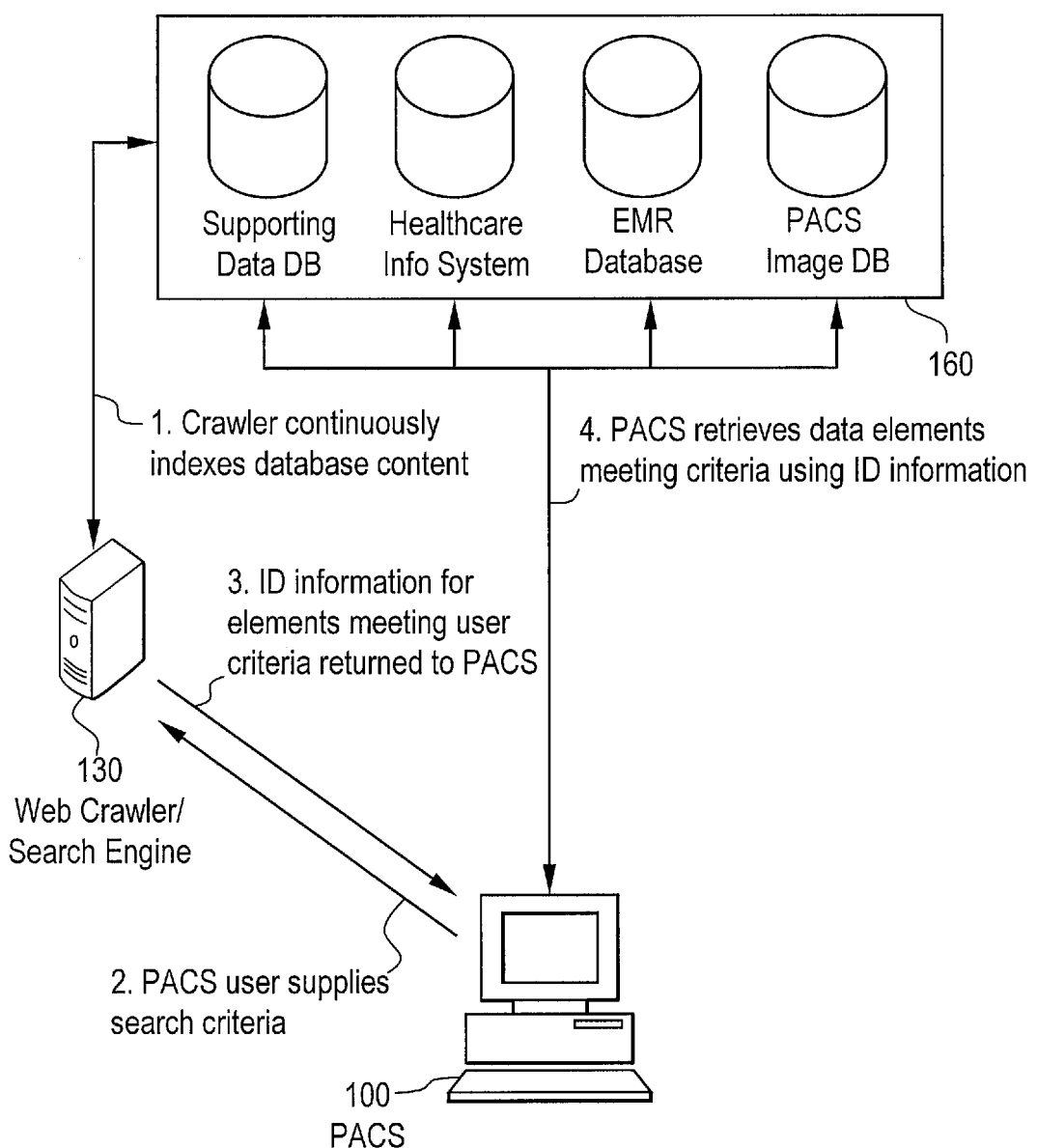
FIG. 1 illustrates a flow diagram of a process for searching and viewing medical images.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an exemplary flow diagram of a process for searching and viewing medical images. A Picture Archiving and Communication System ("PACS") 100 is provided to interact with various databases 160 or healthcare information systems. In certain embodiments, the PACS 100 may interact with only one database. In other embodiments, the PACS 100 may interact with multiple databases and healthcare information systems, each healthcare information system potentially having multiple databases of its own.

In certain embodiments, a web crawler, or search engine 130, interacts with both the PACS 100 and the databases 160 to continuously index database content. For example, images in the databases 160 may be continuously updated with labels identifying aspects of the data, such as information pertaining to whether the images have been previously accessed or viewed. In the depicted embodiment, the search engine 130 is exterior to the PACS 100, but in certain embodiments the search engine 130 may be a component of the PACS 100.

Whether the search engine 130 is a component of, or separate from the PACS 100, the search engine 130 automatically searches patient files in the various databases 160 for information pertaining to whether or not images within the patient files have previously been accessed or viewed.

Figure 2:
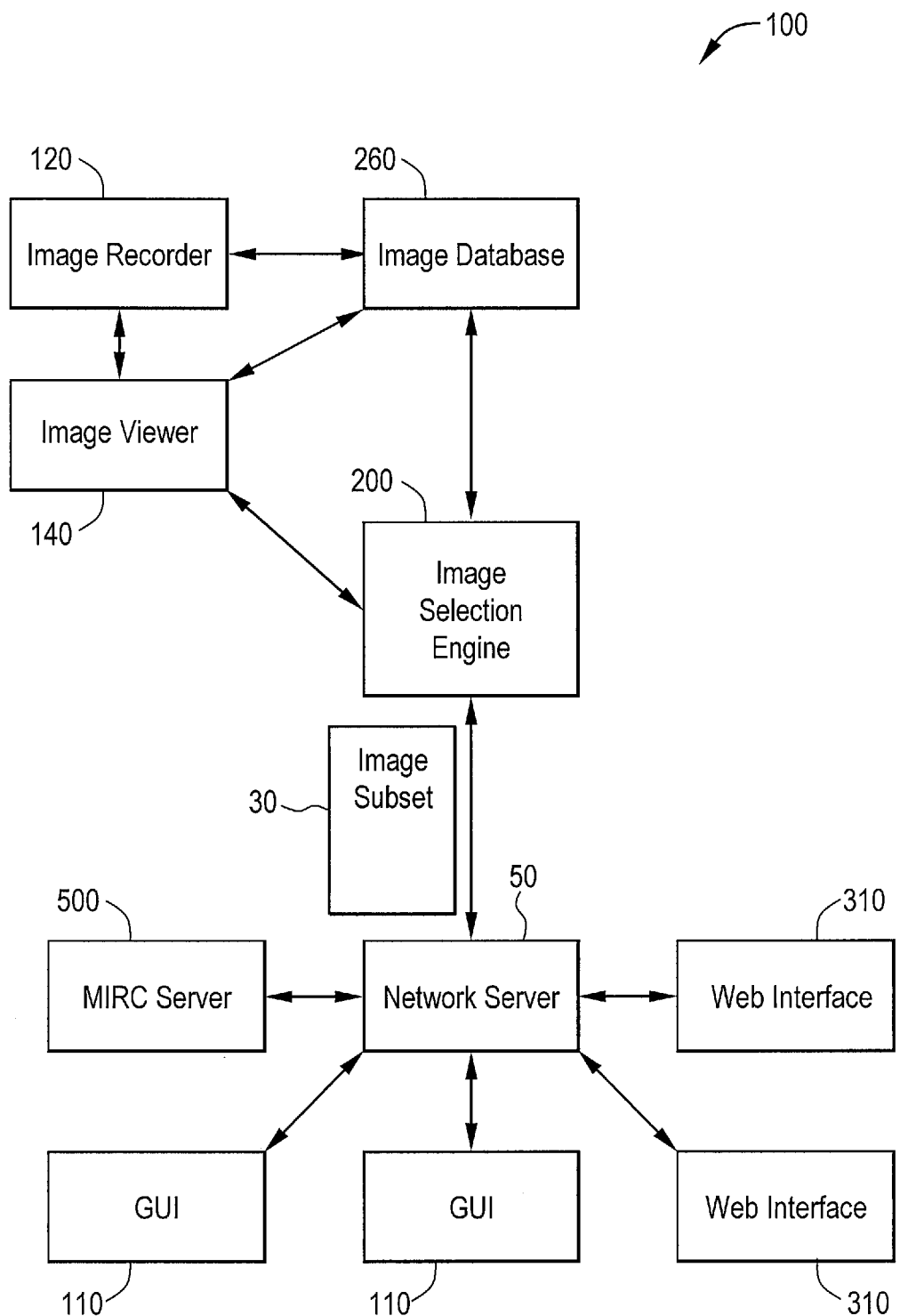
FIG. 2 illustrates a system block diagram of certain components of a method for navigating medical images.

FIG. 2 depicts an embodiment of a system for navigating medical images 170. In certain embodiments, the system for navigating medical images 170 may be located within a PACS such as the PACS 100 of FIG. 1. In certain embodiments, the system for navigating medical images 170 may be external from but in communication with the PACS 100. For example, the system for navigating medical images 170 may only need to interact with the PACS 100 in order to retrieve images and supporting data stored in the PACS 100.

In certain embodiments, a radiologist may use the system for navigating medical images 170 of FIG. 2 to examine and review medical images of a patient file. In certain embodiments, the system for navigating medical images 170 comprises an image recorder 120 such as a radiology scanner or an x-ray scanner. A medical practitioner, for example, a radiologist, may record images using the image recorder 120 and store them within an image database 260. During the interpretation process, the medical practitioner may view and examine the images using an image viewer 140. In certain embodiments, the practitioner may view and study the images as they are recorded using the image viewer 140. In certain embodiments, the image viewer 140 may be a part of a user interface such a graphical user interface ("GUI") 110 on a computer workstation.

In certain embodiments, the system for navigating medical images 170 will not have an image recorder; rather the images will be produced by components external to the system and then forwarded to the system for navigating medical images 170. For example, the system for navigating medical images 170 may not be able to access the image recorder 120 itself, instead only having access to images sent to the system for navigating medical images 170 by the PACS 100.

Because patient files may contain several hundred or thousand images, an image selection engine 200 may be provided so that a practitioner may browse only images that he or she has not previously accessed or viewed. The image selection engine 200 may include an image labeler 210 (FIG. 3) that automatically labels images in the database 260 upon accessing by the user with a "previously viewed" label. The image selection engine 200 may select images that have not previously been accessed by selecting only images that lack the "previously viewed" label. This allows the user to browse only images that he or she has not previously viewed to avoid duplication. It also allows the user to more easily make sure that each image has been viewed at least once.

Figure 3:
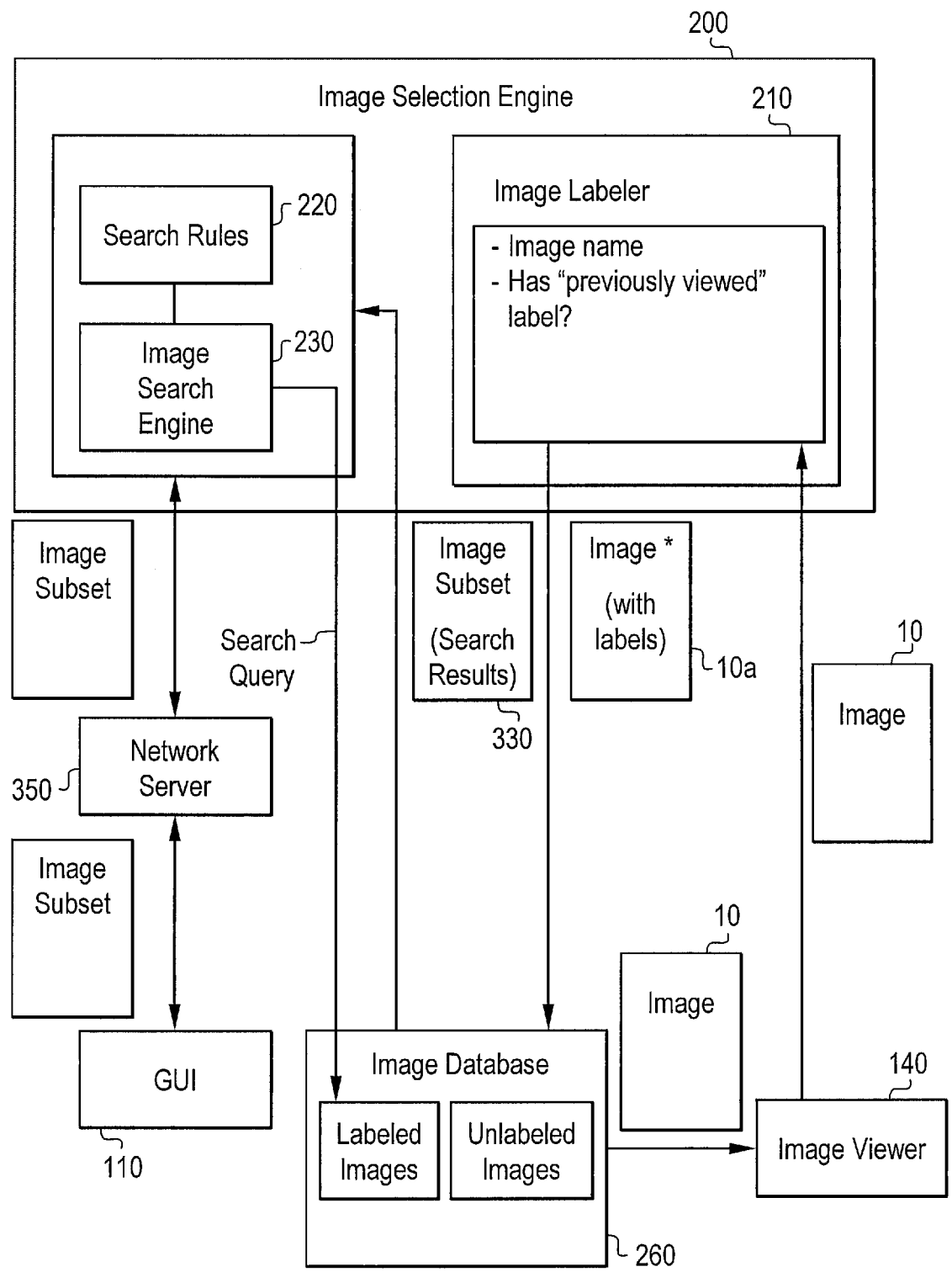
FIG. 3 illustrates a system block diagram of certain components of a method for navigating medical images.

FIG. 3 depicts a block diagram of an exemplary image selection engine in operation with an image viewer and an image database. The image viewer 140 draws an image 10 from the image database so that a user such as a medical practitioner may view the image. In certain embodiments the image viewer 140 may be a GUI, such as GUI 110. The image labeler 210 operates as a component of the image selection engine 200 and records and labels the image 10 with a "previously viewed" label the first time it is accessed through the image viewer 140.

Working with the image labeler 210 in the image selection engine 200 is an image search engine 230 component. The image search engine 230 is governed by a set of search engine rules 220 and operates to produce the image subset 330. For example, the search engine rules 220 may indicate that the image subset 330 should be composed of all of the images that lack the "previously viewed" label. Alternatively, the search engine rules 220 may indicate that the image subset 330 should be composed of all of the images that include the "previously viewed" label In certain embodiments, a user may access the image subset 330 via the GUI 110 via a computer workstation. In certain embodiments, the GUI 110 may be the same device or workstation as the image viewer 140. For example, during the interpretation process a practitioner may view the images from the database 260 through GUI 110, while the image labeler 210 applies labels to the image based on the user's accessing the image via the GUI 110 as it would if the user used image viewer 140.

In certain embodiments, the GUI may be connected to the image subset 330 and, therefore the image selection engine 200 and the image database 260, via a network server 350 that may provide access to the PACS 100 for multiple user interfaces 110 or workstations. The network server 350 may be any type of known network including a local area network (LAN), a wide area network (WAN), an intranet, or a global network (e.g., the internet). For example, a user may access the image subset 330 via the internet from a home computer with a GUI 110, or from a computer terminal at a hospital.

Figure 4:
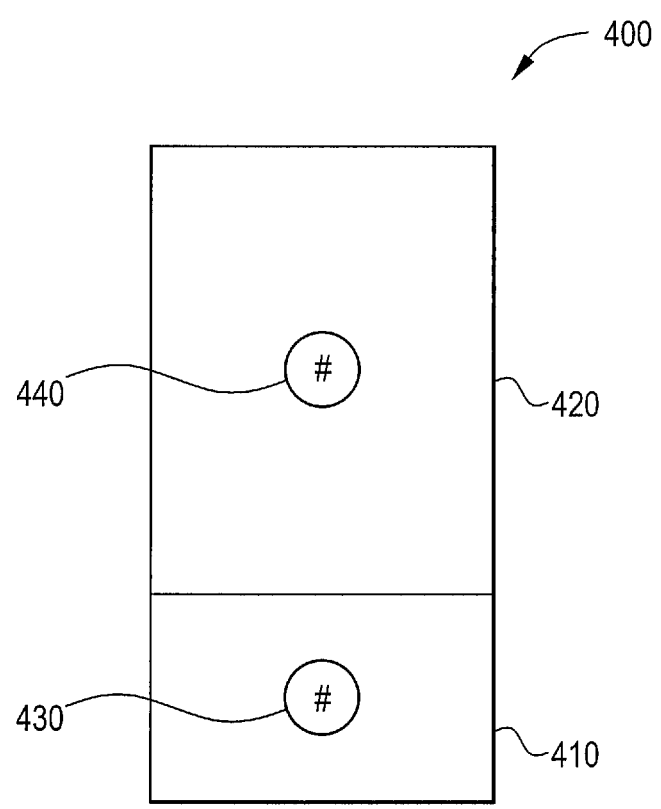
FIG. 4 illustrates a graphical meter for representing which images have and have not been accessed or viewed and for offering a navigation device to the images that have not been viewed.

FIG. 4 depicts a graphical meter 400 that may be used in certain embodiments. The graphical meter 400 may appear in a corner of the image viewer 140. The graphical meter 400 may include a first portion 410 representing the images that have already been accessed (e.g. the images that include the "previously viewed" label) and a second portion 420 representing the images that have not yet been accessed (e.g. the images that lack the "previously viewed" label).

The graphical meter 400 may also include image counters 430 and 440 that display the current number of images in each category: those with the "previously viewed" label and those without the label. For example, the image counter 430 may display the number of images that have already been accessed, which are represented by the first portion 410, while the image counter 440 may display the number of images that remain to be accessed, which are represented by the second portion 420.

In certain embodiments, the first and second portions 410 and 420 may be sized with respect to one another in proportion to the number of images they represent. For example, if a patient file includes 1000 images and 250 images have been viewed while 750 images have not yet been viewed, the first portion 410 may be one third the size of the second portion 420.

The first portion 410 and second portion 420 may be displayed in different colors to provide easily-discernable contrast. For example, the first portion 410 may be depicted in blue while the second portion 420 may be depicted in red.

The first and second portions 410 and 420 may each be clickable through the use of hyperlinks. For example, clicking the first portion 410 may direct a user to the images that have already been viewed while clicking the second portion 420 may direct a user to the images that have not already been viewed. In certain embodiments, clicking the second portion 420 may take a user to a folder containing all of the images that lack the "previously viewed" label. In certain embodiments, clicking the second portion 420 may take a user directly to the first image in a series of images that lacks the "previously viewed" label.

Components of systems 100 and 200 may be implemented in software, hardware and/or firmware and may be implemented individually and/or in a variety of combinations.

Certain embodiments of the present application provide a technical effect of automatically labeling accessed or viewed images upon accessing or viewing. Certain embodiments provide a technical effect of introducing a graphical meter that shows which images have and have not been accessed or viewed, and that offers a navigation device to quickly launch images that have not been viewed.

Those skilled in the art will appreciate that the embodiments disclosed herein may be applied to the formation of any clinical system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A system for navigating a plurality of medical images, said system comprising:
   an interface displaying a plurality of medical images of a patient file stored in an image database,
   an image labeler automatically providing a label for each of said plurality of medical images the first time that said each of said plurality of medical images is viewed by a user at said interface, said label being attached to said each of said plurality of viewed medical images;
   an image search engine automatically searching said plurality of medical images of said patient file based on said label and identifying a first subset of said plurality of medical images comprising any medical image that does not have said label and identifying a second subset of said plurality of medical images comprising any medical image that has said label; and a graphical meter representing said first and second subsets of medical images, said graphical meter being displayed on said interface and automatically displaying a first number of the medical images in the first subset of said plurality of medical images and a second number of the medical images in the second subset of said plurality of medical images based on said label, wherein the plurality of medical images are to be dynamically re-indexed as images are being viewed and wherein said graphical meter is to be dynamically updated to represent the updated first and second numbers resulting from the re-indexing.

2. The system for navigating the plurality of medical images of claim 1, wherein said graphical meter illustrates the proportion of said plurality of medical images that do not contain said label to images that do contain said label.

3. The system for navigating the plurality of medical images of claim 1, wherein said graphical meter contains a hyperlink pointing to one of said plurality of medical images that does not contain said label.

4. The system for navigating the plurality of medical images of claim 1, wherein said graphical meter contains a hyperlink pointing to a folder containing at least one of said first subset and said second subset of medical images.

5. The system for navigating the plurality of medical images of claim 1, wherein said graphical meter contains a hyperlink pointing to a folder containing only those of said plurality of medical images that do not contain said label.

6. The system for navigating the plurality of medical images of claim 1, further comprising an image viewer for accessing, viewing and editing said plurality of medical images from said image database.

7. The system for navigating the plurality of medical images of claim 1, wherein said system operates on a picture archiving and communication system.

8. The system for navigating the plurality of medical images of claim 1, wherein said interface comprises a web interface.

9. A system for navigating a plurality of medical images, said system comprising:

an interface displaying a plurality of medical images of a patient file stored in an image database to a user, an image identifier automatically providing a not previously viewed image label to each of said plurality of medical images that has not previously been displayed on said interface and automatically providing a previously viewed image label to each of said plurality of medical images that has been displayed on said interface;

an image search engine automatically indexing said plurality of medical images of said patient file for said image labels and identifying first and second subsets of said plurality of medical images, said first subset containing any medical image that comprises said not previously viewed image label, said second subset containing any medical image that comprises said previously viewed image label; and a graphical meter representing said first and second subsets of said plurality of medical images, said graphical meter being displayed on said interface and automatically displaying a first number of the medical images in the first subset of said plurality of medical images and a second number of the medical images in the second subset of said plurality of medical images based on said label, wherein the plurality of medical images are to be dynamically re-indexed as images are being viewed and wherein said graphical meter is to be dynamically updated to represent the first and second numbers resulting from the re-indexing.

10. The system for navigating the plurality of medical images of claim 9, wherein said graphical meter illustrates the proportion of said plurality of medical images that contain said not previously viewed image label to images that contain said previously viewed image label.

11. The system for navigating the plurality of medical images of claim 9, wherein said graphical meter contains a hyperlink pointing to one of said plurality of medical images that contains said not previously viewed image label.

12. The system for navigating the plurality of medical images of claim 9, wherein said graphical meter contains a hyperlink pointing to said first subset.

13. The system for navigating the plurality of medical images of claim 9, wherein said graphical meter contains a hyperlink pointing to a folder containing said first subset.

14. The system for navigating the plurality of medical images of claim 9, further comprising an image viewer for accessing, viewing and editing said plurality of medical images from said image database.

15. The system for navigating the plurality of medical images of claim 9, wherein said system operates on a picture archiving and communication system.

16. A system for navigating a plurality of medical images, said system comprising:

an interface displaying a plurality of medical images of a patient file stored in an image database, an image identifier automatically providing a not previously viewed image label to each of said plurality of medical images that has not previously been displayed on said interface and automatically providing a previously viewed image label to each of said plurality of-medical images that has been displayed on said interface;

an image search engine automatically indexing said plurality of medical images of said patient file for said image labels and identifying first and second subsets of said plurality of medical images, said first subset containing any medical image that comprises said not previously viewed image label, said second subset containing any medical image that comprises said previously viewed image label; and a graphical meter representing said first and second subsets of said plurality of medical images, said graphical meter being displayed on said interface and automatically displaying a first number of the medical images in the first subset of said plurality of medical images and a second number of the medical images in the second subset of said plurality of medical images based on said label, wherein the plurality of medical images are to be dynamically re-indexed as images are being viewed and wherein said graphical meter is to be dynamically updated to represent the first and second numbers resulting from the re-indexing;

wherein said system operates on a picture archiving and communication system.

* * * * *